US006337427B1

(12) United States Patent
Alario et al.

(10) Patent No.: US 6,337,427 B1
(45) Date of Patent: *Jan. 8, 2002

(54) PROCESS FOR ISOMERIZING AROMATIC CUTS CONTAINING EIGHT CARBON ATOMS USING A CATALYST CONTAINING A ZEOLITE WITH AN EUO TYPE STRUCTURE

(75) Inventors: Fabio Alario, Neuilly sur Seine; Jean-François Joly, Lyons; Julia Magne-Drisch, Vilette de Vienne; Elisabeth Merlen; Eric Benazzi, both of Chatou; Sylvie Lacombe, Rueil Malmaison, all of (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/287,622

(22) Filed: Apr. 7, 1999

(30) Foreign Application Priority Data

Apr. 8, 1998 (FR) ............................................. 98 04506

(51) Int. Cl.$^7$ ................................................. C07C 5/00
(52) U.S. Cl. ........................ 585/319; 585/481; 585/482; 585/478; 585/477; 208/133
(58) Field of Search .................................. 585/319, 481, 585/422, 478, 477; 208/133

(56) References Cited

U.S. PATENT DOCUMENTS

| 3,577,475 A | * | 5/1971 | Csicery et al. ............... 260/668 |
| 4,062,903 A | * | 12/1977 | Jacobson .................... 260/668 |
| 4,593,138 A | * | 6/1986 | Casci et al. .................. 585/481 |

FOREIGN PATENT DOCUMENTS

| EP | 0 051 318 | * | 5/1982 | |
| JP | 7/5016/780 | * | 6/1975 | ............. C07C/5/24 |
| WO | 96/16004 | * | 5/1996 | |

* cited by examiner

*Primary Examiner*—Helane E. Myers
(74) *Attorney, Agent, or Firm*—Millen, White, Zelano & Branigan, P.C.

(57) ABSTRACT

A process for isomerising aromatic compounds containing eight carbon atoms is described in which the catalyst used contains at least one zeolite with structure type EUO and a group VIII element. In FIG. 1, the feed to be isomerised is introduced into reactor R via line 1. This fresh feed is enriched via lines 6 and 11 with a mixture containing at least one compound selected from the group formed by paraffins containing eight carbon atoms, benzene, toluene and naphthenes containing eight carbon atoms. Hydrogen is added via line 15.

19 Claims, 1 Drawing Sheet

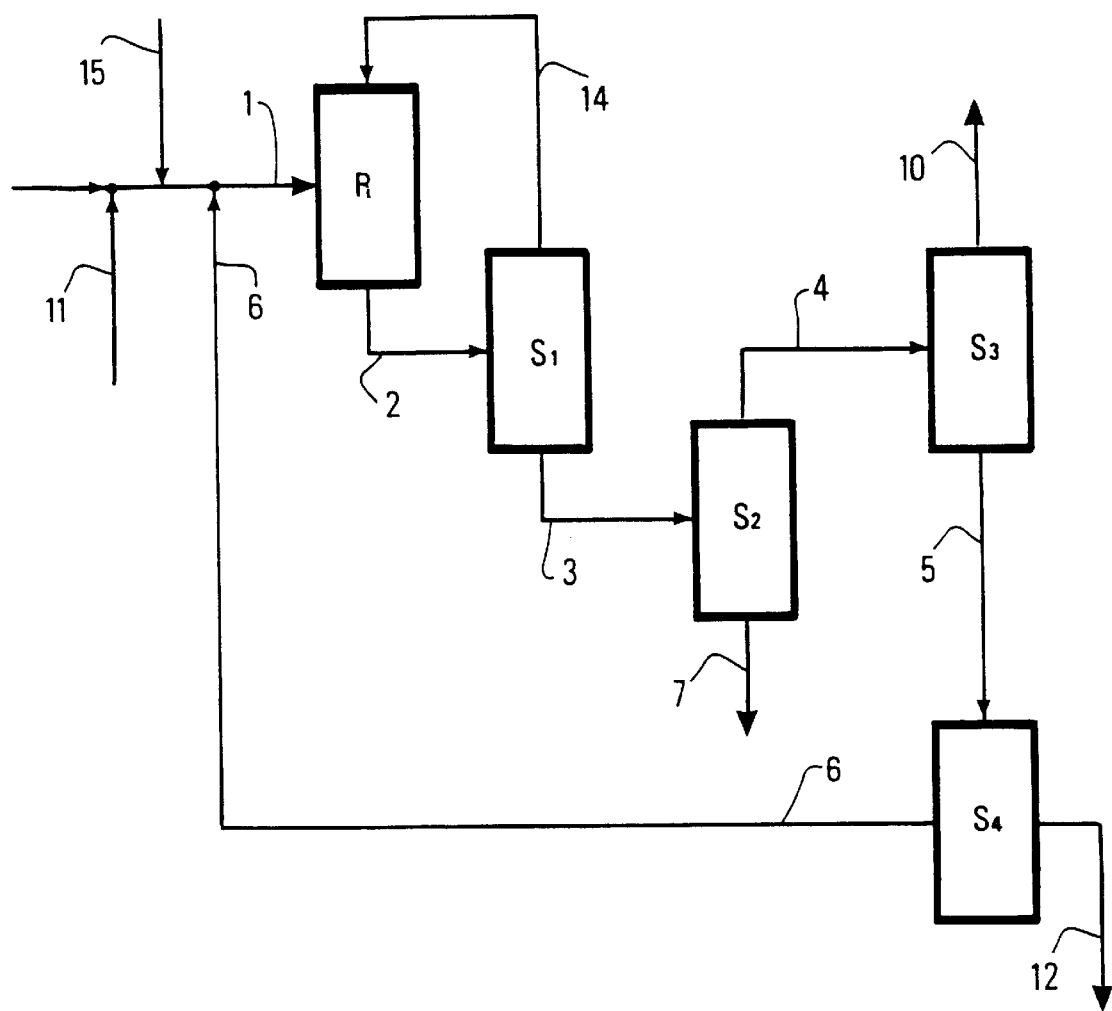

PROCESS FOR ISOMERIZING AROMATIC CUTS CONTAINING EIGHT CARBON ATOMS USING A CATALYST CONTAINING A ZEOLITE WITH AN EUO TYPE STRUCTURE

The present invention relates to processes for isomerising aromatic compounds containing eight carbon atoms. More particularly, the invention relates to a process for isomerising aromatic compounds containing eight carbon atoms in which the catalyst used containing a zeolite with structure type EUO and an element from group VIII of the periodic table (Handbook of Chemistry and Physics, 1964–1965).

Different zeolites corresponding to structure type EUO have been described in the prior art, examples being EU-1 zeolite described in European patent EP-A-0 042 226, TPZ-3 zeolite described in EP-A-0 051 318 and ZSM-50 zeolite described in U.S. Pat. No. 4,640,829.

More specifically, the present invention provides a process for isomerising aromatic compounds containing eight carbon atoms, in which a catalyst is used which contains at least one zeolite with structure type EUO and at least one metal or compound of a metal from group VIII and in which at least one compound with a boiling point of about 80° C. to about 135° C. other than the aromatic compounds containing eight carbon atoms is introduced into the reaction zone with the feed containing the compound or compounds to be isomerised and the hydrogen necessary for the reaction. The group VIII metal is normally selected from noble metals or compounds of noble metals from group VIII and in particular, platinum or palladium is used, or a compound of at least one of these metals, preferably platinum or a platinum compound.

The process of the present invention has a number of advantages over the prior art, including: a reduction in the loss of aromatic compounds containing eight carbon atoms through secondary side reactions of dismutation, transalkylation, hydrogenation and cracking.

In known processes for isomerising aromatic compounds containing eight carbon atoms, a feed which is generally low in para-xylene with respect to the thermodynamic equilibrium of the mixture (i.e., in which the amount of para-xylene is substantially lower than that of the mixture at thermodynamic equilibrium at the temperature under consideration, this mixture comprising at least one compound selected from the group formed by meta-xylene, ortho-xylene, para-xylene and ethylbenzene), and generally rich in ethylbenzene with respect to this same mixture at thermodynamic equilibrium is introduced into a reactor containing at least one catalyst, under suitable pressure and temperature conditions to obtain from the reactor outlet a composition of aromatic compounds containing eight carbon atoms which is as close as possible to the composition of said mixture at thermodynamic equilibrium at the temperature of the reactor.

The para-xylene and optionally ortho-xylene, which are the desired isomers as they are of great importance in particular for the synthetic fibre industry, are then separated from this mixture. The meta-xylene and ethylbenzene can then be recycled to the isomerisation reactor inlet so as to increase the production of para-xylene and ortho-xylene. When ortho-xylene is not to be recovered, it is recycled with the meta-xylene and ethylbenzene.

However, there are a number of problems associated with isomerising aromatic compounds containing eight carbon atoms per molecule, caused by secondary reactions. Thus in addition to the principal isomerisation reaction, hydrogenation reactions are observed, such as hydrogenation of aromatic compounds to naphthenes, and naphthene ring opening reactions which lead to the formation of paraffins containing at most the same number of carbon atoms per molecule as the naphthenes from which they are formed. Cracking reactions are also observed, such as paraffin cracking which leads to the formation of light paraffins, typically containing three to five carbon atoms per molecule, also dismutation and transalkylation reactions which lead to the production of benzene, toluene, aromatic compounds containing nine carbon atoms per molecule (for example trimethylbenzenes) and heavier aromatic compounds.

All together, those secondary reactions are highly deleterious to the yields of the desired products.

The quantity of secondary products formed (primarily naphthenes typically containing 5 to 8 carbon atoms, paraffins typically containing 3 to 8 carbon atoms, benzene, toluene, aromatic compounds containing 9 or 10 carbon atoms per molecule) depends on the nature of the catalyst and the operating conditions of the isomerisation reactor (temperature, partial pressures of hydrogen and hydrocarbons, feed flow rate).

In conventional processes for isomerising aromatic compounds containing eight carbon atoms, a mixture of xylenes and ethylbenzene is brought into contact with a suitable catalyst, generally containing at least one group VIII noble metal and a zeolite, in order to bring the mixture of aromatic compounds containing eight carbon atoms to a composition which is as close as possible to the composition corresponding to thermodynamic equilibrium at the temperature under consideration.

The Applicant has now discovered that, surprisingly, a process for isomerising aromatic compounds containing eight carbon atoms in which a catalyst is used which contains at least one zeolite with a structure type EUO and at least one metal or a compound of a metal from group VIII, and in which at least one compound with a boiling point of about 80° C. to about 135° C. other than the aromatic compounds containing eight carbon atoms is introduced into the reaction zone with the feed containing the compound or compounds to be isomerised and the hydrogen necessary for the reaction, has much better performances than in prior art processes.

In the process of the present invention, the catalyst contains at least one zeolite with structure type EUO, and at least one metal or compound of a metal from group VIII, and thus has the advantage of being carried out in a lower temperature range, at lower partial pressures of hydrogen and at higher HSVs (weight of feed/weight of catalyst/hour).

Preferably, a catalyst is used which contains a zeolite with structure type EUO, for example EU-1 zeolite and platinum. This catalyst contains at least one zeolite with structure type EUO, at least partially in its acid form, this zeolite comprising silicon and at least one element T selected from the group formed by aluminium, iron, gallium and boron, preferably aluminium and boron, and in which the global Si/T atomic ratio is about 5 to 100, preferably about 5 to 80, and more preferably about 5 to 60. This catalyst also comprises at least one matrix (or binder), and at least one metal or compound of a metal from group VIII of the periodic table. This catalyst also optionally comprises at least one metal or compound of a metal selected from the group formed by metals or compounds of metals from groups IIIA and IVA of the periodic table, and optionally sulphur or at least one sulphur compound. The metal is usually selected from the group formed by tin and indium.

The matrix is generally selected from the group formed by natural clays (for example kaolin or bentonite), synthetic clays, magnesia, aluminas, silicas, silica-aluminas, titanium oxide, boron oxide, zirconia, aluminium phosphates, titanium phosphates, and zirconium phosphates, preferably from elements of the group formed by aluminas and clays. This matrix may be a simple compound or a mixture of at least two of these compounds.

The zeolite with structure type EUO is at least partially, preferably almost completely, in its acid form, i.e., in its hydrogen ($H^+$) form.

The weight content of this zeolite is 1% to 90%, preferably 3% to 60%, more preferably 4% to 40%, with respect to the total catalyst weight.

This catalyst also contains at least one matrix, or binder, providing the complement to 100% in the catalyst.

The process for isomerising aromatic compounds containing eight carbon atoms of the present invention is carried out at a temperature of about 300° C. to 500° C., preferably about 320° C. to 450° C., and more preferably about 350° C. to 420° C., at a partial pressure of hydrogen of about 0.3 to 1.5 MPa, preferably about 0.4 to 1.2 MPa, at a total pressure of about 0.45 to 1.9 MPa, preferably about 0.6 to 1.5 MPa, and at an HSV (weight of feed/weight of catalyst/hour) of about 0.25 $h^{-1}$ to 30 $h^{-1}$, preferably about 1 $h^{-1}$ to 10 $h^{-1}$, and usually 2 $h^{-1}$ to 6 $h^{-1}$.

An examination of the literature shows that recycling certain constituents contained in the effluent from the isomerisation reactor to the inlet t that reactor has been envisaged with a view to minimising the production of secondary products.

As an example, U.S. Pat. Nos. 3,553,276, 3,558,173 and 4,255,606 recommend adding certain compounds to the feed to be treated, in order to reduce the loss due to secondary products.

Thus U.S. Pat. No. 3,553,276 describes an apparatus in which toluene is recycled so that its concentration is kept at double the concentration which would be obtained without that recycling.

U.S. Pat. No. 3,558,173 describes recycling naphthenes containing eight carbon atoms produced by hydrogenation of the corresponding aromatic compounds.

In the description in U.S. Pat. No. 4,255,606, 1% to 10% by weight with respect to the total feed of an aliphatic hydrocarbon containing at least five carbon atoms is introduced into the reaction zone with or without adding toluene. This addition can be accomplished by recycling. The hydrocarbon introduced can also be a precursor of n-pentane.

The isomerisation process of the present invention comprises introducing into the reaction zone, with the feed containing the compounds to be isomerised and the hydrogen required for the reaction, at least one compound with a boiling point of about 80° C. to 135° C. and more particularly at least one compound selected from the group formed by: paraffins containing eight carbon atoms per molecule, benzene, toluene, and naphthenes containing eight carbon atoms.

At least one compound selected from the group formed by paraffins containing eight carbon atoms per molecule, benzene, toluene, and naphthenes containing eight carbon atoms is added to the feed to be isomerised, in the form of a recycle, in the form of fresh compound or in the form of a recycle and fresh compound, in quantities such that the percentage by weight of compound added with respect to the total feed entering the reactor is normally:

the percentage by weight of paraffins containing eight carbon atoms in the optional case when these are added to the feed is about 0.1% to 10%, preferably about 0.2% to 2%;

the percentage by weight of naphthencs containing eight carbon atoms in the optional case when these are added to the feed is about 0.5% to 15%, preferably about 2% to 10%;

the percentage by weight of toluene in the optional case when it is added to the feed is about 0.01% to 5%, preferably about 0.01% to 3%;

the percentage by weight of benzene in the optional case when it is added to the feed is about 0.01% to 5%, preferably about 0.01% to 1%.

When a plurality of compounds are added, the percentage by weight of total compounds added represents about 0.01% to 20%, normally about 2% to 15%, with respect to the total feed which enters the reactor. In a preferred implementation of the invention, at least one naphthene is added.

In a preferred implementation of the invention, at least two different compounds are introduced into the reaction zone, each with a boiling point of about 80° C. to 135° C. More particularly, at least one naphthene and at least one paraffin containing eight carbon atoms are introduced. In a further variation, all of the compounds contained in this liquid fraction with boiling points of about 80° C. to 135° C. are introduced without separating them. These compounds may originate from recycling a liquid fraction leaving the reactor.

FIG. 1 shows a simple embodiment of the process of the invention.

In this FIGURE, the feed containing the mixture of aromatic compounds containing eight carbon atoms per molecule to be isomerised is introduced into reactor R via a line 1. Before being injected into isomerisation reactor R, this feed to be isomerised is enriched in at least one compound selected from the group formed by paraffins containing eight carbon atoms, benzene, toluene and naphthenes containing eight carbon atoms. These additions are carried out by means of a recycle via line 6 and by adding fresh compounds via line 11. Substantially pure hydrogen is added via a line 15.

After reacting, the effluent is sent to a separation zone $S_1$ via a line 2. In $S_1$, the hydrogen contained in the effluent is isolated and recycled to the reactor inlet via a line 14, the remainder of the effluent being sent to a separation zone $S_2$ via a line 3. In separation zone $S_2$, the reaction products are separated into two fractions. A light fraction which contains the paraffins, naphthenes and the lightest aromatic compounds including benzene and toluene is sent to a separation zone $S_3$ via a line 4. The other heavier fraction comprising aromatic compounds containing at least 8 carbon atoms is evacuated from the apparatus via a line 7. From this fraction, the desired products, in particular para-xylene, will be extracted after successive separation steps.

In separation zone $S_3$, hydrocarbons containing one to seven carbon atoms —which are evacuated via line 10—are separated from the phase containing the paraffins containing eight carbon atoms, naphthenes containing eight carbon atoms, benzene and toluene. This mixture is sent to a separation zone $S_4$ via line 5. In separator $S_4$, the quantities of paraffins containing eight carbon atoms, benzene, toluene and naphthenes containing eight carbon atoms which are to be recycled are selected, and the mixture to be recycled is then sent via a line 6 upstream of the reactor where it enriches the feed to be isomerised. A line 12 is provided to evacuate the portion of the mixture comprising paraffins containing eight carbon atoms, naphthene containing eight carbon atoms, benzene and toluene which are not to be recycled.

The following examples illustrate the invention without limiting its scope.

The following notation was used in the examples: "C1–C4 paraffins" for paraffins containing 1 to 4 carbon atoms; "C8 paraffins" for paraffins containing eight carbon atoms; and "C6 naphthenes", "C7 naphthenes" and "C8 naphthenes" for naphthenes containing 6, 7 and 8 carbon atoms respectively. "C9+ aromatics" is used for aromatic compounds containing at least 9 carbon atoms.

EXAMPLE 1
(In Accordance with the Invention)

The catalyst used in this Example was prepared as follows.

The starting material was a zeolite with structure type EUO, EU-1 zeolite, as synthesised, comprising an organic template, silicon and aluminium, with a global Si/Al atomic ratio of 13.6, and a sodium content of about 1.5% with respect to the weight of dry EU-1 zeolite, corresponding to an atomic ratio Na/Al of 0.6.

This EU-1 zeolite first underwent dry calcining at 550° C. in a stream of air for 6 hours. The solid obtained then underwent three ion exchange steps in a 10 N $NH_4NO_3$ solution at about 100° C. for 4 hours per exchange step.

After these treatments, the EU-1 zeolite in its $NH_4$ form had a global Si/Al atomic ratio of 18.3, and a sodium content with respect to the weight of dry EU-1 zeolite of 50 ppm by weight.

The EU-1 zeolite was then formed by extrusion with an alumina gel to obtain, after drying and calcining in dry air, support S1 constituted by extrudates 1.4 mm in diameter which contained 10% by weight of EU-1 zeolite in its H form and 90% of alumina.

Support S1 obtained underwent anion exchange with hexachloroplatinic acid in the presence of a competing agent (hydrochloric acid), to introduce 0.3% by weight of platinum with respect to the catalyst. The moist solid was then dried at 120° C. for 12 hours and calcined in a dry air stream at 500° C. for 1 hour.

Catalyst C1 obtained contained 10.0% by weight of EU-1 zeolite in its H form, 89.7% of alumina and 0.29% of platinum.

This catalyst was used under the following operating conditions: a total pressure of 0.9 MPa, a temperature of 380° C. and an HSV of 3 $h^{-1}$.

The liquid effluent leaving the reactor was distilled so as to recover the fraction with a distillation range of 80° C. to 135° C. This fraction was then added to the feed to be isomerised. The mixture obtained was used as a feed for the reactor.

The compositions of the feed and the products obtained are shown in Table 1 below:

TABLE 1

| Compounds | Feed (weight %) | Products (weight %) |
| --- | --- | --- |
| C1–C4 paraffins | 0 | 0.53 |
| i-pentane | 0 | 0.05 |
| n-pentane | 0 | 0.12 |
| benzene | 0.04 | 0.11 |
| toluene | 0.53 | 0.65 |
| ortho-xylene | 21.85 | 19.04 |
| meta-xylene | 51.63 | 40.81 |
| para-xylene | 2.63 | 17.41 |
| ethylbenzene | 14.22 | 11.45 |
| C6 naphthenes | 0.14 | 0.12 |
| C7 naphthenes | 0 | 0.17 |
| C8 paraffins | 0.23 | 0.36 |

TABLE 1-continued

| Compounds | Feed (weight %) | Products (weight %) |
| --- | --- | --- |
| C8 naphthenes | 8.56 | 8.99 |
| C9+ aromatics | 0.17 | 0.18 |

EXAMPLE 2
(Not in Accordance with the Invention)

The starting zeolite was a mordenite in its sodium form, with an Si/Al ratio of 5.2 and a unit cell volume of 2.794 $nm^3$. The zeolite underwent three ion exchange steps in a 10 N $NH_4NO_3$ solution at about 100° C. for 4 hours. The solid obtained contained 25 ppm of sodium.

This zeolite in its hydrogen form was then formed by extruding with an alumina gel to obtain, after drying and calcining in dry air, a catalyst containing 15% by weight of mordenite zeolite in its hydrogen form and 85% by weight of alumina.

This catalyst underwent anion exchange with hexachloroplatinic acid in the presence of a competing agent (hydrochloric acid), to introduce 0.3% by weight of platinum with respect to the catalyst. The moist solid was then dried at 120° C. for 12 hours and calcined in a dry air stream at 500° C. for 1 hour. The catalyst obtained contained 15.0% by weight of mordenite zeolite in its H form, 84.7% of alumina and 0.29% of platinum.

This catalyst was used under the same operating conditions as those described for Example 1.

In order to compare the performances of catalysts based on EU-1 zeolite and mordenite, the same feed was used in Example 2 as that used in Example 1, Table 1.

The compositions of the feed and the products obtained are shown in Table 2 below.

TABLE 2

| Compounds | Feed (weight %) | Products (weight %) |
| --- | --- | --- |
| C1–C4 paraffins | 0 | 0.263 |
| i-pentane | 0 | 0 |
| n-pentane | 0 | 0.078 |
| benzene | 0.04 | 0.294 |
| toluene | 0.53 | 1.075 |
| ortho-xylene | 21.85 | 18.977 |
| meta-xylene | 51.63 | 42.142 |
| para-xylene | 2.63 | 16.505 |
| ethylbenzene | 14.22 | 10.405 |
| C6 naphthenes | 0.14 | 0.118 |
| C7 naphthenes | 0 | 0.233 |
| C8 paraffins | 0.23 | 0.414 |
| C8 naphthenes | 8.56 | 8.2 |
| C9+ aromatics | 0.17 | 1.3 |

The results of Table 2 above clearly show the significance of using a catalyst based on a zeolite with structure type EUO.

The para-xylene content in the effluent was higher, and was 17.41% by weight when using the process in the presence of a catalyst containing a zeolite with structure type EUO of the invention instead of 16.50% by weight when using a mordenite based catalyst.

The yield of aromatic compounds containing eight carbon atoms+naphthenes containing eight carbon atoms obtained in the presence of a catalyst containing a zeolite with structure type EUO was 98.8%, compared with 97.31% obtained with a mordenite based catalyst. The process of the present invention carried out in the presence of a catalyst based on a zeolite with structure type EUO led to a gain in the activity and selectivity compared with a reference system based on mordenite.

EXAMPLE 3
(In Accordance with the Invention)

The catalyst of Example 1 was used.

The catalyst was used under the following conditions: a total pressure of 9 bars absolute, a temperature of 385° C. and an HSV of 3 h$^{-1}$.

The feed to be converted was a mixture of aromatic compounds containing eight carbon atoms and naphthenes containing eight carbon atoms.

The composition by weight of the feed and the products obtained are shown in Table 3.

TABLE 3

| Compounds | Feed (weight %) | Products (weight %) |
| --- | --- | --- |
| C1–C4 paraffins | 0 | 0.51 |
| i-pentane | 0 | 0.14 |
| n-pentane | 0 | 0.06 |
| benzene | 0 | 0.07 |
| toluene | 0 | 0.38 |
| ortho-xylene | 23.85 | 19.41 |
| meta-xylene | 53.38 | 42.22 |
| para-xylene | 1.49 | 18.5 |
| ethylbenzene | 13.26 | 9.47 |
| C6 naphthenes | 0 | 0.04 |
| C7 naphthenes | 0 | 0.11 |
| C8 paraffins | 0 | 0.21 |
| C8 naphthenes | 8.02 | 8.52 |
| C9+ aromatics | 0 | 0.37 |

EXAMPLE 4
(Not in Accordance with the Invention)

The catalyst of Example 2 was used.

The catalyst was used under the same operating conditions as those used in Example 3.

In order to be able to compare the performances of the catalysts based on EU-1 zeolite and mordenite, the same feed was used in Example 4 as that shown in Table 3 of Example 3.

The compositions by weight of the feed and the products obtained are shown in Table 4.

TABLE 4

| Compounds | Feed (weight %) | Products (weight %) |
| --- | --- | --- |
| C1–C4 paraffins | 0 | 0.42 |
| i-pentane | 0 | 0.16 |
| n-pentane | 0 | 0.05 |
| benzene | 0 | 0.19 |
| toluene | 0 | 0.68 |
| ortho-xylene | 23.85 | 19.43 |
| meta-xylene | 53.38 | 42.38 |
| para-xylene | 1.49 | 17.37 |
| ethylbenzene | 13.26 | 9.54 |
| C6 naphthenes | 0 | 0.08 |
| C7 naphthenes | 0 | 0.16 |
| CS paraffins | 0 | 0.26 |
| C8 naphthenes | 8.02 | 7.99 |
| C9+ aromatics | 0 | 1.29 |

The results of Table 4 above clearly show the significance of using a catalyst based on a zeolite with structure type EUO.

The amount of para-xylene in the effluent was higher, and was 18.50% by weight when using the process in the presence of a catalyst containing a zeolite with structure type EUO of the invention, instead of 17.37% by weight when using the catalyst based on mordenite.

The yield of aromatic compounds containing eight carbon atoms and naphthenes containing eight carbon atoms obtained in the presence of a catalyst containing a zeolite with structure type EUO was 98.1%, compared with 96.7% obtained with a mordenite based catalyst. The process of the present invention carried out in the presence of a catalyst based on a zeolite with structure type EUO led to a gain in the activity and selectivity compared with a reference system based on mordenite.

What is claimed is:

1. A process comprising catalytically isomerising aromatic compounds containing eight carbon atoms, wherein the catalyst used contains at least one zeolite with an EUO structure and at least one metal or a compound of a metal from group VIII, and hydrogen and a recycle stream consisting essentially of compounds with a boiling point of about 80° C. to about 135° C. other than said aromatic compounds containing eight carbon atoms is introduced into the reaction zone with the feed containing the eight carbon atom aromatic compound or compounds to be isomerized, withdrawing an isomerizate from the reaction zone, separating said isomerizate to remove compounds having boiling points below about 80° C. and above about 135° C., and recycling at least a fraction of the resultant isomerizate as said recycle stream.

2. A process for isomerising aromatic compounds containing eight carbon atoms according to claim 1, wherein the zeolite with structure EUO contained in the catalyst is selected from the group formed by EU-1 zeolites, TPZ-3 zeolites and ZSM-50 zeolites.

3. A process for isomerising aromatic compounds containing eight carbon atoms according to claim 1, wherein the catalyst used comprises at least one matrix, at least one group VIII element and at least one zeolite with EUO structure, said zeolite containing silicon and at least one element T selected from the group formed by aluminium, iron, gallium and boron, such that the global Si/T atomic ratio is about 5 to 100, said zeolite also being at least partially in its acid form.

4. A process for isomerising aromatic compounds containing eight carbon atoms according to claim 1, wherein the zeolite with an EUO structure contained in the catalyst is an EU-1 type zeolite.

5. A process for isomerising aromatic compounds containing eight carbon atoms according to claim 1, wherein it is carried out at a temperature of about 300° C. to 500° C., at a partial pressure of hydrogen of about 0.3 MPa to 0.15 MPa, at a total pressure of about 0.45 to 1.9 MPa and at an HSV (weight of feed/weight of catalyst/hour) of about 0.25 to 30 h$^{-1}$.

6. A process for isomerising aromatic compounds containing eight carbon atoms according to claim 1, wherein the recycle mixture comprises at least one compound with a boiling point of about 80° C. to 135° C. selected from the group consisting of paraffins containing eight carbon atoms, naphthenes containing eight carbon atoms, toluene and benzene.

7. A process for isomerising aromatic compounds containing eight carbon atoms according to claim 1, wherein compounds with a boiling point of about 80° C. to 135° C. are introduced to the reaction zone, in the form of recycled compounds or in the form of a mixture of fresh and recycled compounds.

8. A process for isomerising aromatic compounds containing eight carbon atoms according to claim 6, wherein paraffins containing eight carbon atoms are introduced in an amount of about 0.1% to 10% with respect to the total feed entering the reactor.

9. A process for isomerising aromatic compounds containing eight carbon atoms according to claim 6, wherein naphthenes containing eight carbon atoms are introduced in an amount of about 0.5% to 15% with respect to the total feed entering the reactor.

10. A process for isomerising aromatic compounds containing eight carbon atoms according to claim 6, wherein toluene is introduced in an amount of about 0.01% to 5% with respect to the total feed entering the reactor.

11. A process for isomerising aromatic compounds containing eight carbon atoms according to claim 6, wherein benzene is introduced in an amount of about 0.01% to 5% with respect to the total feed entering the reactor.

12. A process for isomerising aromatic compounds containing eight carbon atoms according to claim 5, wherein the zeolite with an EUO structure contained in the catalyst is an EU-1 zeolite.

13. A process for isomerising aromatic compounds containing eight carbon atoms according to claim 6, wherein the zeolite with an EUO structure contained in the catalyst is an EU-1 zeolite.

14. A process for isomerising aromatic compounds containing eight carbon atoms according to claim 8, wherein the zeolite with an EUO structure contained in the catalyst is an EU-1 zeolite.

15. A process for isomerising aromatic compounds containing eight carbon atoms according to claim 9, wherein the zeolite with an EUO structure contained in the catalyst is an EU-1 zeolite.

16. A process for isomerising aromatic compounds containing eight carbon atoms according to claim 10, wherein the zeolite with an EUO structure contained in the catalyst is an EU-1 zeolite.

17. A process for isomerising aromatic compounds containing eight carbon atoms according to claim 11, wherein the zeolite with an EUO structure contained in the catalyst is an EU-1 zeolite.

18. A process according to claim 1, wherein the recycle mixture comprises at least one acyclic paraffin containing eight carbon atoms per molecule, at least one naphthene containing eight molecules per molecule, benzene and toluene and being devoid of aromatic hydrocarbons containing at least eight carbon atoms per molecule and (b) paraffinic hydrocarbons containing 1–7 carbon atoms per molecule.

19. A process for isomerising aromatic compounds containing eight carbon atoms according to claim 18, wherein the zeolite with an EUO structure contained in the catalyst is an EU-1 zeolite.

* * * * *

UNITED STATES PATENT AND TRADEMARK OFFICE
CERTIFICATE OF CORRECTION

PATENT NO. : 6,337,427 B1
DATED : January 8, 2002
INVENTOR(S) : Fabio Alario et al.

It is certified that error appears in the above-identified patent and that said Letters Patent is hereby corrected as shown below:

Title page,
Inventors: reads "Lyons" should read -- Lyon --
Item [30], Foreign Application Priority Data, reads "98 04506" should read -- 98 04526 --

Signed and Sealed this

Sixth Day of May, 2003

JAMES E. ROGAN
*Director of the United States Patent and Trademark Office*